US00PP12497P2

(12) United States Plant Patent
Utecht

(10) Patent No.: US PP12,497 P2
(45) Date of Patent: Mar. 26, 2002

(54) GERANIUM PLANT NAMED 'FISEYEWI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,009

(22) Filed: Jan. 31, 2001

(51) Int. Cl.[7] ..... A01H 5/00
(52) U.S. Cl. ..... Plt./325
(58) Field of Search ..... Plt./325, 329

(56) References Cited

PUBLICATIONS

Fischer–Schmülling Plant Alliance Catalog featuring 'FISEYEWI' on p. 9 (2001).
Official Gazette of the Community Plant Variety Office Oct. 15, 1999; European Union Application, denomination, decision for 'FISEYEWI'.
German Application for 'FISEYEWI' Sep. 15, 1998.
German Proprosed Denomination for 'FISEYEWI' Aug. 15, 1999.
Plant Varieties Journal, January 2001, No. 38, pp. 47–48 (Canada).
GTITM UPOVROM Citation for 'FISEYEWI' as per QZ PBR 991045; Jul. 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fiseyewi', as described and illustrated, and particularly characterized by the combined features of white to very light pink, semi-double flowers with large pink eyes, semi-spherical umbels on long peduncles, uniform, medium-green foliage, moderately vigorous growth and medium tall, round plant habit.

1 Drawing Sheet

BACKGROUND OF THE INVENTION

The present invention comprises a new and distinct cultivar of geranium plant, botanically known as *Pelargonium zonale,* and hereinafter referred to by the cultivar name 'Fiseyewi'.

'Fiseyewi' is a product of a planned breeding program which had the objective of creating new geranium varieties with bi-colored flowers, intense green foliage, and medium-sized plant habit.

'Fiseyewi' originated from a hybridization made by the inventor Angelika Utecht in a controlled breeding program in Galdar, Gran Canaria, Spain, in 1995.

The female parent was the commercial variety 'Icecrystal' (unpatented), having light violet flowers with large rose-red eyes on petals, and large, grass-green leaves without zonation. The male parent of 'Fiseyewi' was a hybrid seedling, no. 711-4 (unpatented), derived from a cross between 'Fisbluri', U.S. Plant Pat. No. 8,712, and the variety 'Risque' (unpatented). The seedling was characterized by single-type, pink flowers with darker pink eyes, and dark-green foliage without zonation.

'Fiseyewi' was selected as one flowering plant within the progeny of the stated cross by Angelika Utecht in 1996 in a controlled environment in Galdar, Gran Canaria, Spain.

The first act of asexual reproduction of 'Fiseyewi' was accomplished when vegetative cuttings were taken from the initial selection in the fall of 1996 in a controlled environment in Galdar, Gran Canaria, Spain, by, or under the supervision of, Angelika Utecht. Horticultural examination of plants grown from cuttings of the plant initiated in May 1997 in Hillscheid, Federal Republic of Germany, and continuing thereafter, has demonstrated that the combination of characteristics as herein disclosed for 'Fiseyewi' are firmly fixed and are retained through successive generations of asexual reproduction.

'Fiseyewi' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fiseyewi' in combination distinguish this geranium as a new and distinct cultivar:

1. White to very light pink flowers with large pink eyes;
2. Relatively large, semi-spherical inflorescences on long, strong peduncles;
3. Medium green foliage without zonation;
4. Moderately vigorous growth, and medium tall, round plant habit; and
5. Mid season spring flowering response.

Of the many commercial cultivars known to the present inventor, the most similar in comparison to 'Fiseyewi' are the parental variety 'Icecrystal', 'Americana White Splash', U.S. Plant Pat. No. 9,317, and 'BFP-1700', U.S. Plant Pat. No. 11,397.

In comparison to 'Icecrystal', 'Fiseyewi' has similarly shaped flowers with a similar type of markings, but the main flower color is much lighter, white instead of light violet, and its eyes are pink, while those of 'Icecrystal' are a deep purple-pink.

In comparison to 'Americana White Splash', 'Fiseywi' has flowers with a slightly stronger pink hue, somewhat larger eyes, and generally slightly more intense green foliage, peduncles, and sepals, and distinctly taller plant habit.

In comparison to 'BFP-1700', 'Fiseyewi' has larger and lighter, more pink, less reddish markings on petals, and grows distinctly more vigorously.

BRIEF DESCRIPTION OF THE DRAWING

The accompanying photographic drawing shows typical flower and foliage characteristics of 'Fiseyewi' with colors being as true as possible with an illustration of this type. The photographic drawing shows a flowering potted plant.

The measurements were taken in Langley, British Columbia, Canada on Jul. 20, 2000, 15 weeks after planting rooted cuttings into 6 inch pots. The plants had not been pinched.

In the following description color references are made to The Royal Horticultural Society Colour Chart (R.H.S.). The color values were determined indoors from plants developed in a green-house in May 2000 in Hillscheid, Germany.

Classification:

*Botanical.*—A hybrid of the species *Pelargonium zonale* L'Hérit.

*Commercial.*—Zonal geranium, cv. 'FISEYEWI'.

Inflorescence:

*Umbel.*—Shape: semi-spherical. Average diameter: 107 mm. Average depth: 55 mm. Peduncle length: 172 mm. Peduncle color: grass-green, RHS 143 A. Pedicel length: 25 mm. Pedicel color: light green, RHS 143 B, no anthocyanin. Number of flowers per umbel: about 25–30. Lastingness of umbel: Approximately 18 days.

*Corolla.*—Average diameter: 46–47 mm. Form: Weakly semi-double. Shape: Round, slightly cup-shaped. Number of petals: 6–7. Petal size: Upper petals — 25–27 mm in length, 19–21 mm in diameter, lower and inner petals 22–24 mm in length and 20–22 mm in diameter. Petal shape: Oblong to nearly obovate, with the upper end Rounded, attenuate base, margin entire. Color (general tonality from a distance of three meters): White with a light pink hue, and with large pink eyes. Color of upper petals: Coloration between RHS 155 D–65 D. Markings of upper petals: Large eyes, pink, RHS 68 A. Color of lower petals: Coloration between RHS 155 D–65 D. Markings of lower petals: Medium sized eyes, pink, coloration between RHS 68 A–B. Color of lower surface of petal: Mainly white, RHS 155 D, in parts a light pink hue RHS 65 D. Color of sepals: Outer surface: light green, RHS 143 C, inner surface: light green, RHS 144 B. Number of sepals: 5–6. Sepal size: Upper sepal: 11–12 mm in length, 4–5 mm in diameter, Other sepals: 11–12 mm in length, 3 mm in diameter. Sepal shape: Linear to lanceolate, acute tip, base truncate, margin entire. Number of petaloids: 1–2. Petaloid color: Upper surface is very light pink, RHS 65 D to white, RHS 155 D; lower surface is white RHS 155 D.

*Bud:* (*just prior to petals unfolding*).—Shape: Elliptical. Sepal Color (lower part): Green, color varying between RHS 143 A–B. Petal Color (upper part): Cream to very light pink, RHS 158 B or 65 D. Length: 21 mm. Width: 11 mm.

*Reproductive organs.*—Androecium: 7–10 fertile anthers, white filaments, orange pollen. Gynoecium: 5–6 lobed stigma, light pink stigma and white style. Fertility/seed set: Occasionally a few seeds are developed, mainly from late summer to fall. Pollen: Plenty in quantity, color RHS 33 A. Number of pistils per flower: One.

*Spring flow response period.*—In Hillscheid, Germany, 2000, plants had on average 0.9 flowers opened 8 weeks after planting of rooted cuttings.

*Outdoor flower production.*—Medium to rich flowering, the flower count in 2000 in Hillscheid, Germany, indicated about 4 inflorescences per plant in mid May.

*Durability.*—Good stability of flower color, little shattering, fair rain resistance. Lastingness of individual bloom: Approximately 9 days at 18° C. Fragrance: None.

Plant:

*Foliage.*—Form: Kidney-shaped, with open base. Margin: Bicrenated. Size of leaf: 85 mm wide, 50–55 mm long. Base: Open to wide open, cordate. Apex: Rounded, somewhat wavy. Color of upper surface: Medium green, approximately RHS 137 C. Color of lower surface: About RHS 137 D. Color of zonation: Absent. Petiole: 45–55 mm in length, RHS 143 C.

*General appearance and form.*—Stem color: Green, RHS 143 A. Internode length: 15–20 mm. Branching pattern: 5.3 branches. Plant size: 21.5 cm from soil to surface of foliage canopy 35 cm in diameter (15 week-old plants).

Disease/pest resistance/susceptibility: None observed to date.

I claim:

1. A new and distinct cultivar of geranium plant named 'Fiseyewi', as described and illustrated.

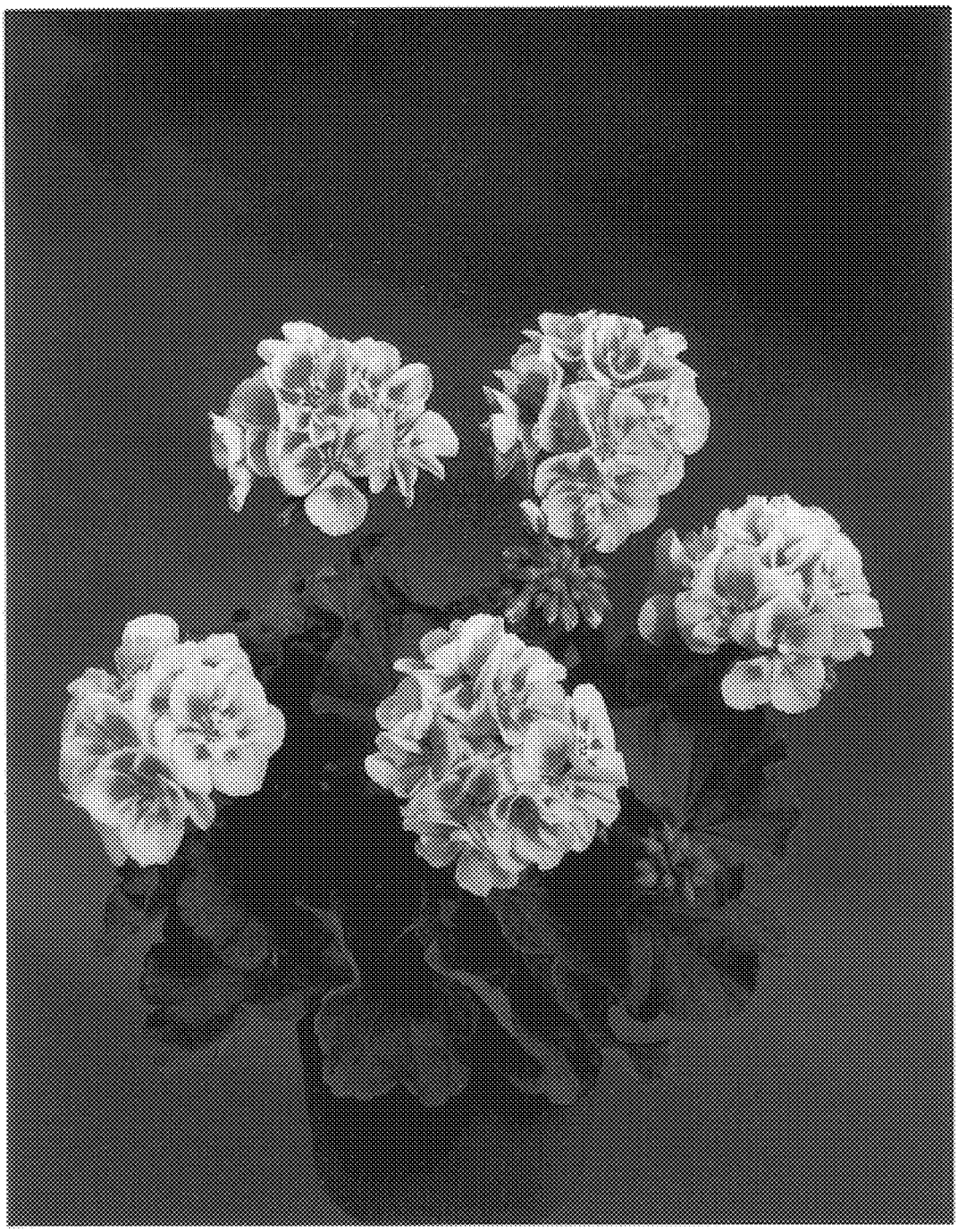

* * * * *